US00PP34035P2

(12) United States Plant Patent
Griffin

(10) Patent No.: US PP34,035 P2
(45) Date of Patent: Mar. 15, 2022

(54) ***MANGAVE* PLANT NAMED 'BARNEY'**

(50) Latin Name: ***Mangave* hybrid**
Varietal Denomination: BARNEY

(71) Applicant: Altman Specialty Plants, Inc, Vista, CA (US)

(72) Inventor: Kelly Griffin, Carlsbad, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/349,337

(22) Filed: Jun. 16, 2021

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 6/12
See application file for complete search history.

*Primary Examiner* — Anne Marie Grunberg
(74) *Attorney, Agent, or Firm* — Cassandra Bright

(57) ABSTRACT

A new and distinct cultivar of *Mangave* plant named 'BARNEY' is disclosed, characterized by a fountain-shaped plant with a moderate to fast growth rate. Foliage has a rich purple coloration and is deeply channeled and recurved. Plants have a moderate growth rate and are slower to flower than other *Mangaves*, resulting in longer lived plants in cultivation. The new variety is an *Mangave*, typically produced as a garden or container plant.

1 Drawing Sheet

Latin name of the genus and species: *Mangave* hybrid.
Variety denomination: 'BARNEY'.

BACKGROUND OF THE INVENTION

The new cultivar is a product of a planned breeding program. The seed parent is a proprietary, unnamed, unpatented *Mangave* hybrid. The pollen parent is a proprietary, unnamed, unpatented *Mangave* hybrid. The crossing was made in July of 2016 at a commercial greenhouse in Vista, Calif. 'BARNEY' was found and selected by the inventor in August of 2017 at the same greenhouse in Vista, Calif.

Asexual reproduction of the new cultivar 'BARNEY' was first performed by tissue culture at a commercial laboratory in Vista, Calif. in August of 2017. 'BARNEY' has since produced several generations and has shown that the unique features of this cultivar are stable and reproduced true to type.

SUMMARY OF THE INVENTION

The cultivar 'BARNEY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BARNEY'. These characteristics in combination distinguish 'BARNEY' as a new and distinct *Mangave* cultivar:

1. Rich purple coloration of leaves in full sun.
2. Fountain shaped growth habit.
3. Moderate to fast growth rate.
4. Slower to flower than other *Mangaves* which translates to longer lived plants in cultivation. Flowering not observed to date.
5. Deep channeled recurved leaves.

PARENTAL COMPARISON

Plants of the new cultivar 'BARNEY' are similar to the seed parent in most horticultural characteristics. However, plants of the new variety differ from the seed parent in the following:

1. The new variety forms a larger plant than the seed parent.
2. The new variety has stronger recurved leaves than the seed parent.
3. The new variety has denser purple coloration than the seed parent.

Plants of the new cultivar 'BARNEY' are similar to the pollen parent in most horticultural characteristics. However, plants of the new variety differ in the following:

1. The new variety has upright, recurved, channeled leaves on found on the pollen parent.
2. The new variety produces a fountain shaped plant, not found in the pollen parent.
3. The new variety has a different purple coloration than the pollen parent.

COMMERCIAL COMPARISON

'BARNEY' can be compared to the commercial variety *Mangave* 'Purple People Eater' U.S. Plant Pat. No. 29,949. The two *Mangave* varieties are similar in most horticultural characteristics; however, the new variety differs in the following:

1. The new variety forms a more fountain-shaped plant than this comparator.
2. The new variety has more greyed-purple coloration to the leaves than this comparator.

3. The new variety has foliage which is more strongly recurved and channeled than this comparator.

BRIEF DESCRIPTION OF THE PHOTOGRAPH

The accompanying photograph illustrates in full color typical plants of 'BARNEY' grown in a greenhouse in Vista, Calif. This plants are approximately 16 months old, shown in 1-gallon containers. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2007 edition, except where general terms of ordinary dictionary significance are used. The following observations and measurements describe 'BARNEY' plants in a commercial greenhouse in Vista, Calif. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Mangave* hybrid 'BARNEY'.

Age of the plant described: About 18 months.

PROPAGATION

Root description: Thick (4 to 8 mm diameter), dense. Near RHS Yellow-White 158C.

Propagation method: Tissue culture.

PLANT

Growth habit: Fountain-shaped rosette.

Container size: 1 gallon.

Height: Approximately 14 cm.

Plant spread: Approximately 30 cm.

Growth rate: Moderate to fast.

Branching characteristics: No branches.

FOLIAGE

Leaf:

*Arrangement*.—Rosette.

*Average length*.—Average 10-12 cm.

*Average width*.—Average 4.0 to 4.5 cm.

*Shape of blade*.—Broad lanceolate to narrow deltate.

*Apex*.—Acuminate, sharp.

*Base*.—Clasping.

*Aspect*.—Strongly recurved and channeled.

*Margin*.—Moderately sharply serrate. Serrations small, about 2 mm to 3 mm tall and about 3 mm wide at base. Regularly spaced about 3 mm apart. Colored near Greyed-Purple N186C flushed N186B.

*Texture of top surface*.—Glabrous, rough.

*Texture of bottom surface*.—Glabrous, rough.

*Quantity of leaves per plant*.—Average 25.

*Color*.—Young foliage upper side: Near RHS Greyed-Green 191B, densely covered with irregularly sized rounded blotches colored near Greyed-Purple N187B and N187C (colors subtly blended together). Blotches about 4 to 8 mm in diameter, densely spaced and overlapping. Purple coloration covers about 60% of the leaf blade. Overall glaucous coloration near Greyed-Purple N187C. Young foliage under side: Near RHS Greyed-Green 191B, densely covered with irregularly sized rounded blotches colored near Greyed-Purple N187B and N187C (colors subtly blended together). Blotches about 4 to 8 mm in diameter, densely spaced and overlapping. Purple coloration covers about 60% of the leaf blade. Overall glaucous coloration near Greyed-Purple N187D. Mature foliage upper side: Near RHS Greyed-Green 191B and 191C, densely covered with irregularly sized rounded blotches colored near Greyed-Purple N187B and N187C (colors subtly blended together). Blotches about 4 to 8 mm in diameter, densely spaced and overlapping. Purple coloration covers about 60% to 80% of the leaf blade. Overall glaucous coloration near Greyed-Purple N187C. Mature foliage under side: Near RHS Greyed-Green 191B and 191C, densely covered with irregularly sized rounded blotches colored near Greyed-Purple N187B and N187C (colors subtly blended together). Blotches about 4 to 8 mm in diameter, densely spaced and overlapping. Purple coloration covers about 60% to 80% of the leaf blade. Overall glaucous coloration near Greyed-Purple N187D. Venation: Linear. Color indistinguishable from leaf blade.

FLOWER

Not observed.

REPRODUCTIVE ORGANS

Not observed.

OTHER CHARACTERISTICS

Seeds and fruits: Not observed.

Temperature tolerance: Tolerates temperatures from approximately 0° to at least 35° C. Low temperature improved if plants are kept dry.

Disease/pest resistance: Neither resistance no susceptibility to normal diseases and pests of *Mangave* observed.

What is claimed is:

1. A new and distinct cultivar of *Mangave* plant named 'BARNEY' as herein illustrated and described.

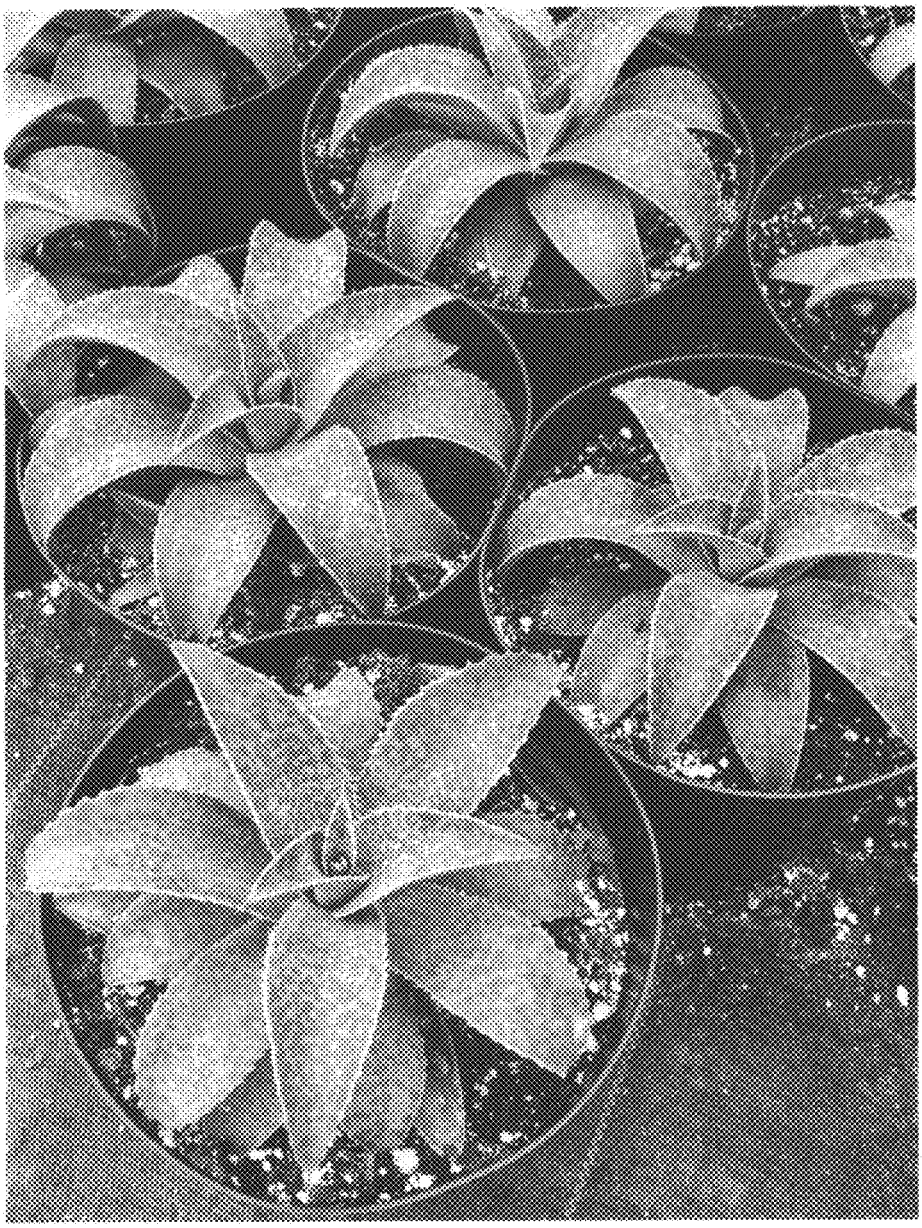

* * * * *